United States Patent [19]

Toth

[11] Patent Number: 4,900,318

[45] Date of Patent: Feb. 13, 1990

[54] ABSORBENT PAD WITH MOISTURE BARRIER

[75] Inventor: Michael R. Toth, Andover, Mass.

[73] Assignee: The Kendall Company, Boston, Mass.

[21] Appl. No.: 59,657

[22] Filed: Jun. 8, 1987

[51] Int. Cl.$^4$ .............................................. A61F 13/16
[52] U.S. Cl. .................................. 604/385.1; 604/378
[58] Field of Search ................. 604/385.1, 385.2, 369, 604/378

[56] References Cited

U.S. PATENT DOCUMENTS 3,349,769 10/1967 Piekarski ............................... 604/365
3,572,342 3/1971 Lindquist .............................. 604/369
4,610,682 9/1986 Kopp ................................... 604/385.1

Primary Examiner—John D. Yasko
Attorney, Agent, or Firm—Alvin Isaacs

[57] ABSTRACT

A disposable pad having leak proof longitudinal sides formed from water impervious barriers disposed longitudinally thereon, between the top sheet and the absorbent pad, and extending to the longitudinal perimeter. A centrally disposed longitudinal section of the top sheet permits entry of fluid into the absorbent pad. The barriers provide envelopes to prevent that fluid from leaking out the sides of the absorbent pad, onto a wearer thereof.

7 Claims, 2 Drawing Sheets

ABSORBENT PAD WITH MOISTURE BARRIER

BACKGROUND OF THE INVENTION (1) Field of the Invention

This invention relates to absorbent pads and more particularly to incontinent briefs and disposable diapers having waterproof crotch seals.

(2) Description of the Prior Art

Minimization of leakage of diapers has been long sought after. A more notable patent in that area is shown in U.S. Patent to Buell, U.S. Pat. No. 3,860,003. In that patent elastic strips are secured to the crotch portions of the diaper and spaced at least three quarters of an inch from the absorbent pad to form elasticized crotch seals for securement over the legs of an infant to prevent loss of fluid from the interior of the diaper along the legs of the infant.

A more recent patent concept is shown in U.S. Pat. No. 4,643,729 to Karami. This patent shows a disposable diaper having elasticized waterproof crotch seals formed from waterproof elastic strips secured to the backing sheet and the absorbent pad and which strips are under tension to eliminate transverse pleats in the crotch area.

BRIEF SUMMARY OF THE INVENTION

The present invention improves upon the prior art diapers. The present invention includes a generally hourglass shaped brief or diaper having a crotch area and portions of greater width defining ears. The absorbent pad or brief comprises a backing sheet of fluid impervious film. The pad may also comprise a top sheet of nonwoven fibers or the like. The backing sheet may be sealed to the top sheet along the peripheral edges thereof by heat or adhesive means. An absorbent pad is disposed between the top sheet and the backing sheet. The pad may generally conform to an hourglass shape. A moisture proof barrier is disposed to cover the sides of the absorbent pad and adjacent to part of the top sheet. The moisture barrier extends along the longitudinal length of the absorbent pad or diaper except across the longitudinal mid portion of the pad or diaper. Each moisture barrier thus forms a pocket extending longitudinally along the length of the absorbent pad, on each side thereof. A further embodiment contemplates the moisture proof barrier extending across the entire top sheet, with only a generally oval shaped central portion being fluid pervious. The moisture proof barrier forms a wall or dam to envelop any fluids contained between the backing sheet and the barrier. Thus it is shown that the absorbent pad with the barrier can contain the liquids absorbed therein and prevent those liquids from extending around the crotch portion and leak from the ears of the absorbent pad.

BRIEF DESCRIPTION OF THE DRAWINGS

The objects and the advantages of the present invention will become more apparent, when viewed in conjunction with the following drawings, in which.

DETAILED DESCRIPTION OF THE PREFERRED EMBODIMENT

Figure 1:
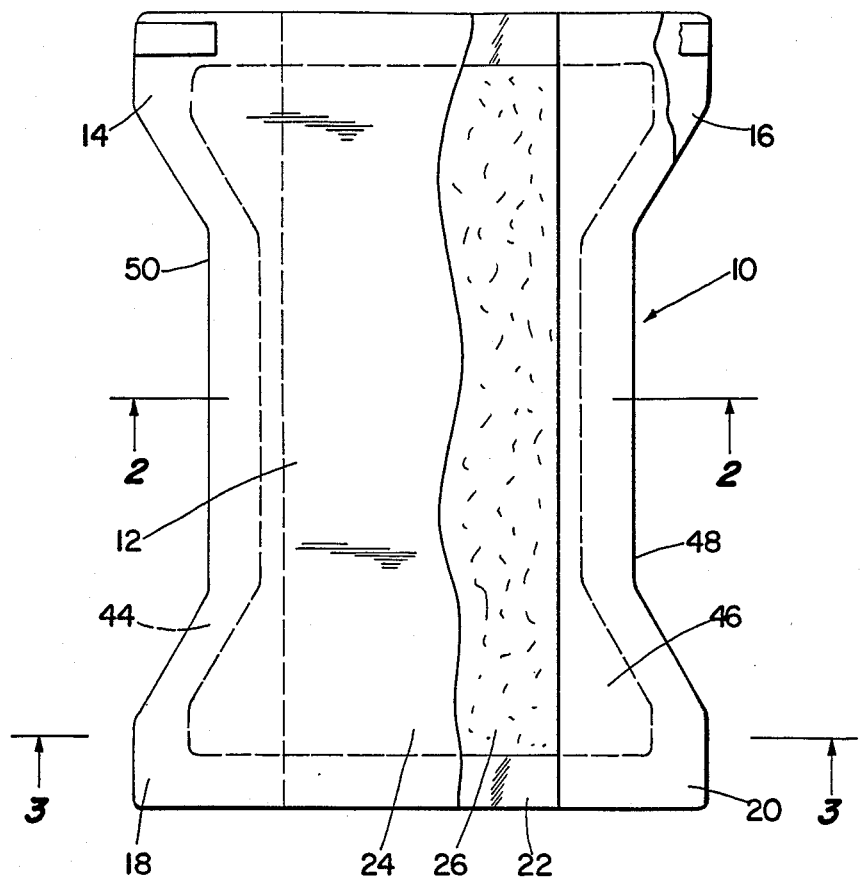
FIG. 1 is a plan view of a diaper constructed in accordance with the principles of the present invention.
Figure 2:
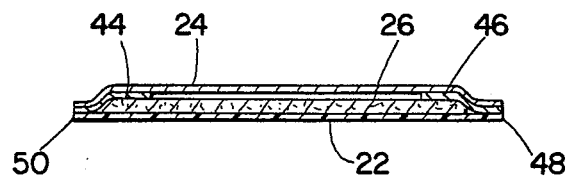
FIG. 2 is a transverse view taken along the lines II—II of FIG. 1.
Figure 3:
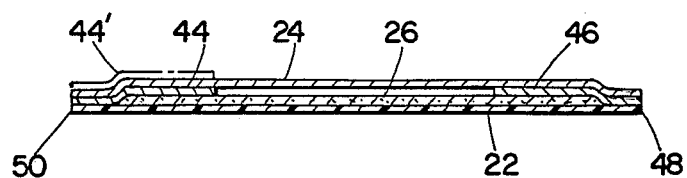
FIG. 3 is a view taken along the lines III—III of FIG. 1.

Referring now the drawings in detail and more particularly to FIG. 1, there is shown a contoured disposable absorbent pad 10 such as an incontinent brief or diaper, constructed in accordance with the principles of the present invention. The absorbent pad 10 of a generally hourglass configuration has a crotch area 12 and four portions of greater width each comprising an ear 14, 16, 18 and 20. The pad 10 includes a backing sheet 22 of a fluid impervious sheet such as polyethylene or polypropylene film. A top sheet 24, preferably of nonwoven or polyethylene or polypropylene fibers is preferably heat sealed by heat or hot melt lines, to the backing sheet along the peripheral edges of the absorbent pad. An inner absorbent pad 26 is disposed between the top sheet 24 and backing sheet 22 and may be made of wood fluff or like absorbent. The inner pad 26 may conform generally to an hourglass configuration. An arrangement of moisture barriers 44 and 46 are disposed longitudinally down the side portions of the absorbent pad 10. The barriers 44 and 46 are each disposed over the inner absorbent pad 26 as shown in FIG. 1. Each barrier is of undivided, single layer construction in order to present a barrier structure of minimum thickness and bulk. The moisture barriers 44 and 46 are placed onto the absorbent pad assembly 10 prior to the top sheet 24 being placed thereon. The moisture barriers 44 and 46 may be comprised of a fluid impervious polyethylene or polypropylene film, or the like. Thus, the backing sheet 22, the moisture barriers 44 and 46, and the top sheet 24 are bonded together along their common periphery so as to form sealed edges 48 and 50. A further embodiment is depicted in phantom lines in FIG. 3, wherein a moisture barrier 44' is shown disposed above the top sheet 24. The moisture barrier 44' in this embodiment could be adhered to the top sheet 24 by known bonding means, which might be similar to that used on the common peripheral edges. A further embodiment may comprise a treating of the top sheet 24 by a known fluid impervious spray or hot melt onto the side portions thereof, so as to duplicate the effect of the fluid impervious barriers with the top sheet 24, alone. The bonding as such, may be done by adhesive or heat bonding, known in the art.

The relationship of the moisture barriers 44 and 46 with the backing sheet 22 is such as to form a pair of longitudinally extending pockets or envelopes into which longitudinal side portions of the inner absorbent pad 26 are disposed. The peripheral sealing of the common edges along the side portions of the absorbent pad 10 entirely along the sides prevents moisture from leaking therepast and down the wearer's leg.

Figure 4:
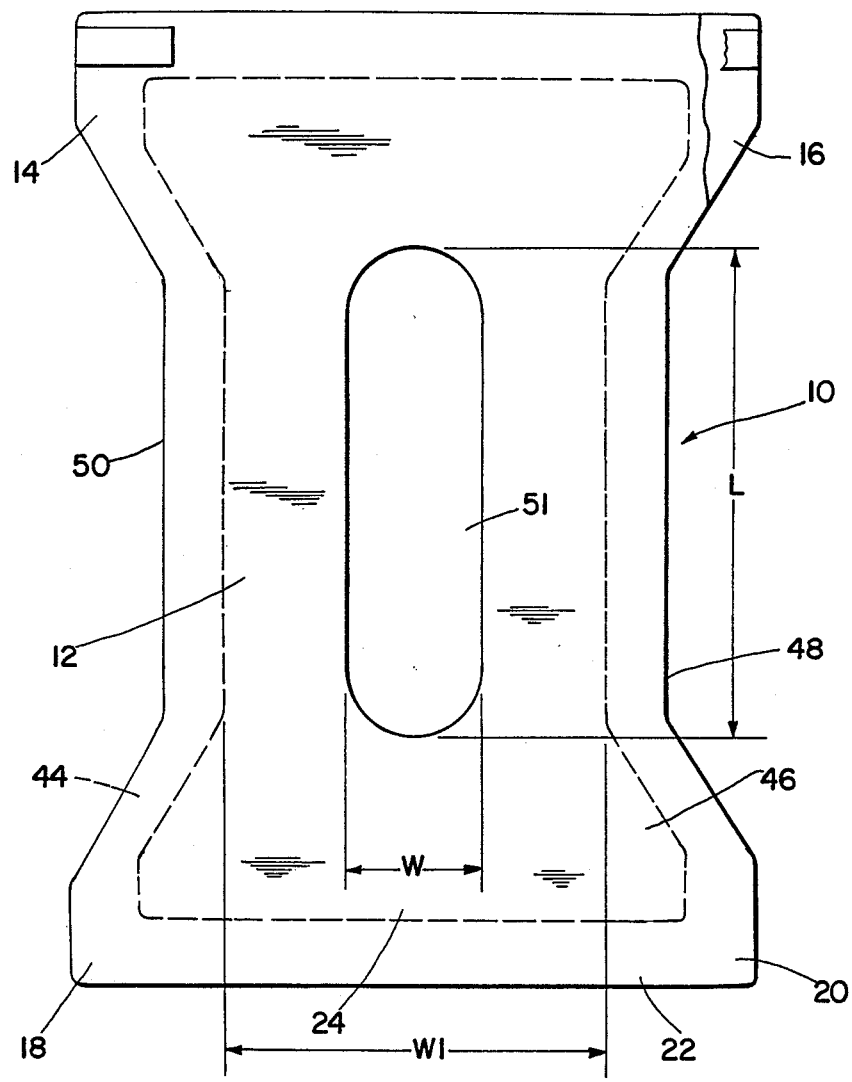
FIG. 4 is a plan view of a diaper in an alternative arrangement.

A further embodiment is shown in FIG. 4, wherein the top sheet 24 is entirely fluid impervious, except for a generally oval shaped central portion 51 which is fluid pervious. The fluid impervious portion of the top sheet 24 may be comprised of polyethylene or polypropylene film or a nonwoven fiber coated with a fluid impervious coating or spray, known in the art. The oval central portion 51 would then comprise an uncoated nonwoven fibrous section. The central portion 51 would extend preferably the length L of the crotch area 12, which for definitional purposes, is recited as one-third the length of the absorbent pad 26, which pad runs the full length of the disposable pad 10. The width W of the central portion 51 is less than 90 percent the width W1 of the absorbent pad 26 at the mid-point of the crotch area 12.

Thus when body fluids pass into the pad 26 those fluids are prevented from passing beyond the periphery of the pad not only in the crotch area but around the front and back portions of the absorbent pad structure 10 itself.

What I claim is:

1. A disposable absorbent pad assembly for use on humans comprising:
   (1) a fluid-impervious backing sheet;
   (2) a fluid-pervious top sheet;
   (3) an absorbent pad disposed between said backing and top sheets; and
   (4) a pair of fluid-impervious barriers arranged between said pad and said top sheet, each said barrier being disposed longitudinally along a longitudinal side portion of said absorbent pad assembly, each said barrier being of undivided, single layer construction to present a barrier structure of minimum thickness and bulk, said barriers thus defining a centrally disposed longitudinally directed fluid-pervious area between said barriers, said barriers, backing sheet and top sheet being bonded together along their common periphery whereby to form sealed edges blocking the escape of fluid along the entire side periphery of said absorbent pad assembly, said barriers and said backing sheet further being characterized as providing a pair of pockets for fluid retention extending longitudinally along the length of said absorbent pad on each side thereof.

2. A disposable pad assembly as recited in claim 1, wherein said backing sheet, said absorbent pad and said top sheet are of an hour-glass configuration, having a narrow portion defining a crotch area, and end portions each having ear areas;
   each of said barriers extending longitudinally through said crotch portion and said ear areas on said pad assembly;
   said barrier and said top sheet and said bottom sheet having a common generally longitudinal perimeter.

3. A disposable pad assembly as recited in claim 2, wherein said common perimeter of said backing sheet, said top sheet and said barrier are adhered together by adhesive means.

4. A disposable pad assembly as recited in claim 3, wherein said adhesive means comprises a heat bonding.

5. A disposable pad assembly as recited in claim 3, wherein said barrier is comprised of a polyethylene film.

6. A disposable pad assembly as recited in claim 3, wherein said barrier is comprised of a polypropylene film.

7. A disposable pad assembly as recited in claim 1, wherein an additional pair of fluid—impervious barriers is applied directly to said top sheet along each longitudinally directed side thereof.

* * * * *